United States Patent [19]

Schach et al.

[11] Patent Number: 5,294,742
[45] Date of Patent: Mar. 15, 1994

[54] PROCESS FOR PREPARING 3,5-DIFLUOROANILINE

[75] Inventors: Thomas Schach, Hofheim am Taunus; Theodor Papenfuhs, Frankfurt am Main, both of Fed. Rep. of Germany

[73] Assignee: Hoechst Atkiengesellschaft, Frankfurt, Fed. Rep. of Germany

[21] Appl. No.: 32,986

[22] Filed: Feb. 18, 1993

[30] Foreign Application Priority Data

Mar. 21, 1992 [DE] Fed. Rep. of Germany ....... 4209208

[51] Int. Cl.$^5$ ............................................. C07C 209/36
[52] U.S. Cl. .................................. 564/417; 568/938; 570/141
[58] Field of Search ................ 568/938; 570/140, 141; 564/417

[56] References Cited

U.S. PATENT DOCUMENTS

| | | | |
|---|---|---|---|
| 2,519,317 | 8/1950 | Kolka et al. | 568/938 |
| 3,634,520 | 1/1972 | Crivello | 568/938 |
| 4,294,988 | 10/1981 | Tull et al. | 568/938 |
| 4,324,914 | 4/1982 | Cordier | 564/417 |
| 4,568,781 | 2/1986 | Effenberger et al. | 568/937 |
| 5,041,674 | 8/1991 | Pews et al. | 568/938 |
| 5,081,288 | 1/1992 | Blank et al. | 564/417 |

FOREIGN PATENT DOCUMENTS

| | | | |
|---|---|---|---|
| 0001825 | 5/1979 | European Pat. Off. | 568/938 |
| 3400418 | 7/1985 | European Pat. Off. | 568/937 |
| 159388 | 10/1985 | European Pat. Off. | 570/141 |
| 355719 | 2/1990 | European Pat. Off. | 570/141 |
| 0460639 | 12/1991 | European Pat. Off. | 568/938 |
| 0497213 | 8/1992 | European Pat. Off. | 570/141 |
| 259529 | 2/1990 | Japan | 570/141 |

OTHER PUBLICATIONS

Finger, G. C., et al., *J. Am. Chem. Soc.* 73:153–155 (1951).

Dickerson, D. R., et al., *Trans. Ill. State Acad. Sci.* 65:75–80 (1972).

"Low Angle Xray Diffraction of Colloidal Gold and Carbon Black", Turkevich et al., Journal of the American Chemical Society, vol. 37, No. 1, pp. 153–155, Jan. 24, 1951.

"Reaction products with Pentachlorobenzene to Potassium Fluoride to Dimethyl Sulfoxide", Dickerson et al., Transactions Illinois Academy of Science, 1971, pp. 75–79.

Chemical Abstracts, vol. 117, No. 23, Dec. 7, 1992, p. 826, Abstract pp. 117:233573, Voker et al.

Chemical Abstracts, vol. 52, No. 22, Abstract No. 19987, Hendrickson et al.

*Primary Examiner*—James H. Reamer
*Attorney, Agent, or Firm*—Connolly and Hutz

[57] ABSTRACT

Process for preparing 3,5-difluoroaniline, wherein
(1) 2,4,5-trichloronitrobenzene is reacted with an alkali metal fluoride in the presence or absence of a polar aprotic solvent at temperatures of about 100° C. to about 250° C., and, after filtering off precipitated salts and fractional distillation of the crude solution,
(2) the resulting 5-chloro-2,4-difluoronitrobenzene is chlorinated with denitration to give 1,3-dichloro-4,6-difluorobenzene in the absence of a Lewis acid or of another chlorination catalyst, using anhydrous chlorine gas at temperatures of about 80° to about 250° C., and
(3) this compound is nitrated to give 2,6-dichloro-3,5-difluoronitrobenzene in oleum with mixed acid (sulfuric acid/nitric acid) at temperatures of about 15° to about 80° C., and
(4) this compound is reduced with hydrogen in the presence of palladium as catalyst and in the presence of an inorganic or organic base at temperatures of about 40° to about 250° C.

20 Claims, No Drawings

PROCESS FOR PREPARING 3,5-DIFLUOROANILINE

The present invention relates to a novel process for preparing 3,5-difluoroaniline, starting from 2,4,5-trichloronitrobenzene and proceeding via 5-chloro-2,4-difluoronitrobenzene, 1,3-dichloro-4,6-difluorobenzene and 2,6-dichloro-3,5-difluoronitrobenzene.

3,5-Difluoroaniline plays an important role as a component in the synthesis of pharmaceutical products, but is also required as an intermediate product in the field of plant protection.

However, the introduction of two fluorine substituents in the 3 and 5 positions relative to an amino or nitro functionality is very difficult to bring about. For this purpose, synthesis alternatives using the technically elaborate and consequently very expensive Balz-Schiemann reaction come into consideration, as well as a further route proceeding via trinitrobenzene as intermediate. As well as unfavorable fluoride yields, very large quantities of byproducts are also to be expected in these methods, while, in addition, elaborate safety precautions are likely to be required (DE-A 34 00 418). A further synthesis alternative proceeds via 2,4-difluoroaniline, which, in a multi-stage reaction sequence, can be transformed into 3,5-difluoroaniline in only moderate yields (Finger G. C.; J. Am. Chem. Soc., 73, 153-155).

There was therefore a need for a novel synthesis route which, based on process stages which are technically simple to manage and using a starting compound which is readily available on the industrial scale, makes it possible to synthesize the desired 3,5-difluoroaniline in high yield.

It has now been found, surprisingly, that 3,5-difluoroaniline can be prepared advantageously and in good yields by (1) reacting 2,4,5-trichloronitrobenzene with an alkali metal fluoride, such as lithium, sodium, potassium, rubidium or cesium fluoride, or mixtures thereof, in the presence or absence of a polar aprotic solvent, such as, for example, dimethylformamide, dimethylacetamide, dimethyl sulfoxide, tetramethylene sulfoxide, dimethyl sulfone, diphenyl sulfoxide, diphenyl sulfone, sulfolane, N-methylpyrrolidone or 1,3-dimethylimidazolin-2-one, in the absence or presence of a phase transfer catalyst at temperatures of about 100° C. to about 250° C., preferably of about 160° C. to about 200° C., and, after filtering off precipitated salts and fractional distillation of the crude solution, (2) chlorinating the resulting 5-chloro-2,4-difluoronitrobenzene with denitration to give 1,3-dichloro-4,6-difluorobenzene in the absence of a Lewis acid or of another chlorination catalyst, using anhydrous chlorine gas at temperatures of about 80° C. to about 250° C., preferably of about 100° C. to about 220° C., and (3) nitrating this compound to give 2,6-dichloro-3,5-difluoronitrobenzene in oleum with mixed acid (sulfuric acid/nitric acid) at temperatures of about 15° C. to about 80° C., preferably of about 20° C. to about 50° C., and (4) reducing this compound with hydrogen, or a hydrogen-supplying compound, in the presence of palladium as catalyst and in the presence of an organic or inorganic base for binding the hydrogen chloride which is formed, at temperatures of about 40° to about 250° C., preferably of about 70° to about 150° C.

Further details of the procedure for the last stage (4), concerning the conversion of the 2,6-dichloro-3,5-difluoronitrobenzene into 3,5-difluoroaniline, are given below:

The palladium which is used as catalyst is expediently employed on a support material. Examples of suitable support materials are calcium carbonate or barium sulfate, but preferably active charcoal.

The catalyst (palladium) may be employed in concentrations of about 0.5 to about 30 percent by weight, based on the support material which is used. The catalyst is expediently used in quantities of about 0.001 to about 50 mmol of palladium per mole of chlorine to be eliminated from the 2,6-dichloro-3,5-difluoronitrobenzene.

Inorganic bases which are used for binding the hydrogen chloride which is formed are ammonia or hydroxides, oxides, carbonates or hydrogen carbonates of alkali metals or alkaline earth metals, or mixtures thereof, such as, for example, the sodium, potassium, calcium or magnesium compounds.

Organic bases which can be employed are nitrogen bases, such as, for example, trialkyl($C_1$–$C_{20}$)amines, where the alkyl groups may be identical or different, for example triethylamine.

The concentration of the base may be selected at will. Aqueous solutions are preferred with concentrations of about 5 to about 50% of the base employed. In this context it is expedient for the concentration of the base to be chosen so that the resultant ammonium chloride, alkali metal chloride or alkaline earth metal chloride still remains completely in solution at the workup temperature.

Hydrogen is preferably employed as reducing agent. However, other reducing agents which can serve as hydrogen suppliers may also be used, such as, for example, hydrazine hydrate, glycols, such as ethylene glycol, polyhydric alcohols, such as glycerol, monohydric aliphatic alcohols, such as methanol or ethanol, or formates.

The latter reaction (stage 4) may be carried out in the presence or absence of atmospheric oxygen.

If hydrogen is used as reducing agent, the reaction is carried out in a hydrogen atmosphere under pressure. In this case, preferred hydrogen pressures are from about 0.1 to about 50 bar.

The reduction may be carried out at temperatures of about 40° to about 250° C., with temperatures of about 70° to 150° C. being preferred. Temperatures which are too low result in a reaction which is slow and incomplete, whereas temperatures which are too high may lead to the elimination of fluoride.

In order to keep the said fluoride elimination, which occurs particularly towards the end of the reaction, as low as possible, the reduction is preferably terminated after 90-95% conversion, and the crude solution thus obtained is fractionally distilled. Incompletely reacted intermediates can then be reused in the subsequent reaction.

The used catalyst resulting from the reaction can be used further without treatment or can be purified using known purification processes, such as, for example, using steam.

More favorable catalyst efficiencies can be achieved through a gradual reduction, by first reducing the nitro group to the amino group at relatively low temperatures within the indicated temperature range and without a base, and subsequently initiating the chlorine elimination by adding a base at a higher temperature within the indicated temperature range.

Besides 3,5-difluoro-2,6-dichloronitrobenzene, mixtures of different dichlorodifluoronitrobenzenes may also be employed as the starting compound in the reduction, in particular mixtures resulting from the nitration of 1,3-dichloro-4,6-difluorobenzene.

Purification of the crude solution obtained after the reduction is preferably effected by steam distillation and/or fractional distillation; where appropriate, purification can be followed by crystallization.

The yield of 3,5-difluoroaniline, based on the immediate precursor 2,6-dichloro-3,5-difluoronitrobenzene, is very good.

By nitration of 1,3-dichloro-4,6-difluorobenzene, the 2,6-dichloro-3,5-difluoronitrobenzene is available after stage 3 in good yields (75–95%) and selectivities (87:12; 3,5-difluoro-2,6-dichloronitrobenzene:2,6-difluoro-3,5-dichloronitrobenzene). (See also Trans. Ill. State Acad. Sci., 65, (1972) 75–80).

As well as pure 1,3-dichloro-4,6-difluorobenzene, mixtures of 1,3-dichloro-4,6-difluorobenzene and 1,3-dichloro-2,4-difluorobenzene may also be used as starting compounds for the nitration. Mixtures of oleum, $H_2SO_4$ and $HNO_3$ which are preferably used for nitrating the 1,3-dichloro-4,6-difluorobenzene are those calculated in such a way that a 95–100% strength sulfuric acid is formed at the end of the reaction. The product (2,6-dichloro-3,5-difluoronitrobenzene) arising from the nitration can be separated off as a liquid phase after diluting the sulfuric acid at temperatures of about 30° to about 45° C. Before the separation, it is expedient for the organic phase to be taken up in an additional solvent. Suitable solvents for this are, for example, toluene, xylene, lower alkanes, ethers and polyethers. After washing to neutrality, the crude solution thus obtained is preferably employed in the subsequent stage without further pre-treatment. Separation of the isomers which have formed, by fractional distillation, is also possible, however.

The 1,3-dichloro-4,6-difluorobenzene which is required as the starting compound for this nitration can be prepared in very good yields by means of stage 2 (action of chlorine on 5-chloro-2,4-difluoronitrobenzene in the absence of a Lewis acid). In this context, the chlorine can be allowed to act on 5-chloro-2,4-difluoronitrobenzene alone or on a mixture of the latter compound and 3-chloro-2,4-difluoronitrobenzene (ratio by weight 85:14). The (denitrating) chlorination can be undertaken both batchwise and continuously, the continuous (denitrating) chlorination being preferred (continuous addition of the 5-chloro-2,4-difluoronitrobenzene or of the said mixture and continuous removal of the 1,3-dichloro-4,6-difluorobenzene formed).

Phase transfer catalysts which may be used in stage 1 (reaction of 2,4,5-trichloronitrobenzene with an alkali metal fluoride in a polar aprotic solvent) are tetraalkyl($C_1$-$C_{18}$)ammonium chlorides or bromides, tetraalkyl($C_1$-$C_{18}$)phosphonium chlorides or bromides, tetraphenylphosphonium chloride or bromide, [(phenyl)$_m$-alkyl($C_1$-$C_{18}$)$_n$]phosphonium chlorides or bromides, where m is=1 to 3, n is=3 to 1 and m+n=4.

The 5-chloro-2,4-difluoronitrobenzene obtained in the first stage can also be prepared in good yields by chlorinating 2,4-difluoronitrobenzene, which is available on an industrial scale, by, for example, mixing 4801 g (30.2 mol) of 2,4-difluoronitrobenzene with 82 g of $FeCl_3$, heating the reaction solution to 80° C., passing chlorine through the solution, terminating the reaction after 78 hours, extracting the reaction solution with sodium sulfite solution, washing to neutrality with water and fractionally distilling.

The 1,3-dichloro-4,6-difluorobenzene obtained in the second stage may also be prepared in good selectivities and yields by chlorinating 1,3-difluorobenzene or 1-chloro-2,4-difluorobenzene.

The examples below serve to illustrate the process according to the invention without limiting it thereto.

EXAMPLE 1

Preparation of 5-chloro-2,4-difluoronitrobenzene 452.8 g (2 mol) of 2,4,5-trichloronitrobenzene, 232.4 g (4.0 mol) of potassium fluoride, 60.8 g (0.4 mol) of cesium fluoride and 632 g of sulfolane are introduced into a 2 l three-necked flask with an internal thermometer, paddle mixer and reflux condenser. The reaction suspension is heated to 160° C. and stirred vigorously at this temperature for 8 hours. Subsequently it is cooled to room temperature, the precipitated salts are filtered off with suction and the crude solution is fractionally distilled.

267.1 g of 5-chloro-2,4-difluoronitrobenzene are obtained, corresponding to a yield of 69% of theory.

EXAMPLE 2

Preparation of 1,3-dichloro-4,6-difluorobenzene 3 kg (15.5 mol) of iron-free, dry 5-chloro-2,4-difluoronitrobenzene are introduced into a 2 l four-necked flask with stirrer, dropping funnel and gas inlet tube and, on top, a column with reflux condenser. After heating the reaction solution to 200° C., chlorine is passed through the solution at a rate of 15 l/h. After 4–6 hours, the solution begins to boil, and after a further 2–4 hours the 1,3-dichloro-4,6-difluorobenzene which is formed can be taken off at the head of the column. At the same time, fresh 5-chloro-2,4-difluoronitrobenzene is added to the reaction in accordance with the quantity of product removed.

The yields of 1,3-dichloro-4,6-difluorobenzene are over 90% of theory, based on reacted 5-chloro-2,4-difluoronitrobenzene.

EXAMPLE 3

Preparation of 2,6-dichloro-3,5-difluoronitrobenzene 475.7 g (2.6 mol) of 1,3-dichloro-4,6-difluorobenzene are suspended in 981.8 g of oleum (20% $SO_3$) in a 2 l four-necked flask with paddle mixer, reflux condenser and 500 ml dropping funnel. Subsequently, 595.7 g of mixed acid (66% $H_2SO_4$/34% $HNO_3$) are slowly added dropwise within 4 hours at such a rate that the reaction temperature does not exceed 30° C. After the addition is complete, stirring of the reaction solution is continued at 30°–40° C. for a further 2 hours, and the solution is then added to 1500 g of ice and brought to 40° C., and the organic phase is separated off. The organic phase is subsequently mixed with 100 g of toluene, treated with $Na_2CO_3$ solution, and washed to neutrality with water. The crude solution thus obtained can be employed in the subsequent stage without further working-up.

633.0 g of crude solution are obtained, of which 547.0 g are crude product (86% of which is 2,6-dichloro-3,5-difluoronitrobenzene) (11% of which is 3,5-dichloro-2,6-difluoronitrobenzene)

The yield of 2,6-dichloro-3,5-difluoronitrobenzene is 79.4% of theory.

EXAMPLE 4

Preparation of 3,5-difluoroaniline 547 g of crude 2,6-dichloro-3,5-difluoronitrobenzene (containing 86% 2,6-dichloro-3,5-difluoronitrobenzene and 13% 3,5-dichloro-2,6-difluoronitrobenzene) in 200 g of toluene and 25 g of Pd/C (5% strength, 50% water content) are introduced into a reaction vessel (autoclave). The mixture of the reaction component is heated to 45° C. Reduction with hydrogen to the corresponding amine then takes place at this temperature. When no further uptake of hydrogen can be observed, the reaction solution is stirred at the same temperature for a further hour, and then cooled to room temperature and mixed with 1064 g of sodium hydroxide solution (20% strength). After heating to 80° C., the dechlorination with reduction takes place until no further uptake of hydrogen can be observed. Subsequently, the catalyst is filtered off with suction from the reaction mixture, and the organic phase is separated off and fractionally distilled.

184.4 g of 3,5-difluoroaniline (yield 69.2% of theory) and 19.8 g of 2,6-difluoroaniline (yield 58.2% of theory) are obtained.

EXAMPLE 5

Preparation of 3,5-difluoroaniline 547 g of crude 2,6-dichloro-3,5-difluoronitrobenzene (containing 86% 2,6-dichloro-3,5-difluoronitrobenzene and 13% 3,5-dichloro-2,6-difluoronitrobenzene) in 100 g of toluene are introduced into a reaction vessel (autoclave) together with 17.5 g of Pd/C (5% strength, 50% water content) and 104.8 g of MgO in 450 g of water. The mixture of the reaction components is heated to 45° C. and reduced with hydrogen at this temperature to the corresponding amine. As the reaction subsides, the temperature is gradually increased to 120°-130° C., as a result of which the hydrogen uptake increases once again and the chlorine atoms which are present are eliminated reductively. After reaction is complete, stirring is continued for a further hour at the same temperature, and the crude solution is then cooled to room temperature and steam-distilled, and the organic phase which is obtained is separated off and fractionally distilled.

Yield: 29.1 g (80.1%) 2,6-difluoroaniline, 237.8 g (89.9%) 3,5-difluoroaniline.

Based on Example 5, the yield over the last three stages is 63.8% of theory.

Based on Example 5, the yield over all the stages is 44% of theory.

We claim:

1. A process for preparing 3,5-difluoroaniline, comprising the following stages:
   (1) reacting 2,4,5-trichloronitrobenzene with an alkali metal fluoride in the presence or absence of a polar aprotic solvent at a temperature in the range of about 100° to about 250° C., and, after filtering off precipitated salt or salts and, if a solvent is present, fractional distillation of the resulting crude solution, or chlorinating 2,4-difluoronitrobenzene, to obtain 5-chloro-2,4-difluoronitrobenzene,
   (2) denitrating with chlorination the resulting 5-chloro-2,4-difluoronitrobenzene to give 1,3-dichloro-4,6-difluorobenzene, said stage 2 being carried out in the absence of a Lewis acid or of another chlorination catalyst, using anhydrous chlorine gas at a temperature in the range of about 80° to 250° C., and
   (3) nitrating the resulting 1,3-dichloro-4,6-difluorobenzene to give 2,6-dichloro-3,5-difluoronitrobenzene, said stage 3 being carried out in oleum with sulfuric acid/nitric acid at a temperature in the range of about 15° to about 80° C., and
   (4) reducing, with elimination of chlorine, the resulting 2,6-dichloro-3,5-difluoronitrobenzene with hydrogen or a hydrogen-supplying compound in the presence of palladium as catalyst and in the presence of an inorganic or organic base at a temperature in the range of about 40° to about 250° C.

2. The process as claimed in claim 1, wherein the reaction in stage 1 is carried out with a fluoride of lithium, sodium, potassium, rubidium or cesium, or a mixture thereof.

3. The process as claimed in claim 1,
   wherein the reaction in stage 1 is carried out at temperatures of about 160° to about 200° C.

4. The process as claimed in claim 1,
   wherein the reaction in stage 1 is carried out in dimethylformamide, dimethylacetamide, dimethyl sulfoxide, tetramethylene sulfoxide, dimethyl sulfone, diphenyl sulfoxide, diphenyl sulfone, sulfolane, N-methylpyrrolidone or 1,3-dimethylimidazolin-2-one as the polar aprotic solvent.

5. The process as claimed in claim 1,
   wherein the reaction in stage 1 is carried out in the presence of a tetraalkyl($C_1$-$C_{18}$)ammonium chloride or bromide, tetraalkyl($C_1$-$C_{18}$)phosphonium chloride or bromide, tetraphenylphosphonium chloride or bromide or [(phenyl)$_m$alkyl($C_1$-$C_{18}$)$_n$]-phosphonium chloride or bromide, where m is=1 to 3, n is=3 to 1 and m+n=4, as a phase transfer catalyst.

6. The process as claimed in claim 1,
   wherein the denitrating chlorination in stage 2 is carried out at temperatures of about 100° to about 220° C.

7. The process as claimed in claim 1,
   wherein the denitrating chlorination in stage 2 is carried out continuously.

8. The process as claimed in claim 1,
   wherein the nitration in stage 3 is carried out with a mixed acid consisting essentially of 66% $H_2SO_4$ and 34% $HNO_3$ in oleum.

9. The process as claimed in claim 1, wherein the nitration in stage 3 is carried out at a temperature in the range of about 20° to 50° C.

10. The process as claimed in claim 1, wherein, in stage 4, said hydrogen-supplying compound is a glycol, a polyhydric alcohol, a monohydric aliphatic alcohol or a formate.

11. The process as claimed in claim 1,
    wherein the reaction in stage 4 is carried out in a hydrogen atmosphere under pressure when hydrogen is used as reducing agent.

12. The process as claimed in claim 11,
    wherein said reaction is carried out in a hydrogen atmosphere under a pressure of about 0.1 to about 50 bar.

13. The process as claimed in claim 1,
    wherein in stage 4 the palladium is employed on a support material.

14. The process as claimed in claim 13, wherein in stage 4 the palladium is employed on calcium carbonate, barium sulfate or active charcoal as the support material.

15. The process as claimed in claim 1, wherein in stage 4 the palladium is used in a quantity of about 0.001 to about 50 mmol per mole of chlorine to be eliminated.

16. The process as claimed in claim 13, wherein in stage 4 the palladium is employed in a concentration of about 0.5 to about 30% by weight, based on the support material used.

17. The process as claimed in claim 1, wherein the reduction in stage 4 is carried out in the presence of ammonia or of an hydroxide, oxide, carbonate or hydrogen carbonate of an alkali metal or of an alkaline earth metal, or a mixture thereof.

18. The process as claimed in claim 1, wherein the reduction in stage 4 is carried out in solution and is terminated after 90 to 95% conversion, and the resulting crude product solution thus obtained is fractionally distilled.

19. The process as claimed in claim 1, wherein:
in stage 2, the resulting 5-chloro-2,4-difluoronitrobenzene to be denitrated with chlorination contains 3-chloro-2,4-difluoronitrobenzene in admixture therewith,
in stage 3, the resulting 1,3-dichloro-4,6-difluorobenzene to be nitrated contains 1,3-dichloro-2,4-difluorobenzene in admixture therewith, and
in stage 4, a dichlorodifluoronitrobenzene other than 3,5-difluoro-2,6-dichloronitrobenzene may be present in addition to the 3,5-difluoro-2,6-dichloronitrobenzene.

20. A process for preparing 3,5-difluoroaniline comprising the following stages:
(1) chlorinating 1,3-difluorobenzene or 1-chloro-2,4-difluorobenzene to obtain give 1,3-dichloro-4,6-difluorobenzene,
(2) nitrating the resulting 1,3-dichloro-4,6-difluorobenzene, in oleum with sulfuric acid/nitric acid at a temperature in the range of about 15° to about 80° C., to give 2,6-dichloro-3,5-difluoronitrobenzene, and
(3) reducing, with elimination of chlorine, the resulting 2,6-dichloro-3,5-difluoronitrobenzene with hydrogen or a hydrogen-supplying compound in the presence of palladium as catalyst and in the presence of an inorganic or organic base at a temperature in the range of about 40° to about 250° C.

* * * * *